US012657696B2

(12) United States Patent
Shafiee et al.

(10) Patent No.: US 12,657,696 B2
(45) Date of Patent: Jun. 16, 2026

(54) DETERMINING LOCATIONS IN REPRODUCTIVE CELLULAR STRUCTURES

(71) Applicants: THE BRIGHAM AND WOMEN'S HOSPITAL, INC., Boston, MA (US); THE GENERAL HOSPITAL CORPORATION, Boston, MA (US)

(72) Inventors: Hadi Shafiee, Boston, MA (US); Charles Bormann, Winchester, MA (US); Manoj Kumar Kanakasabapathy, Boston, MA (US); Prudhvi Thirumalaraju, Watertown, MA (US)

(73) Assignees: THE GENERAL HOSPITAL CORPORATION, Boston, MA (US); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 233 days.

(21) Appl. No.: 18/025,480

(22) PCT Filed: Sep. 13, 2021

(86) PCT No.: PCT/US2021/050050
§ 371 (c)(1),
(2) Date: Mar. 9, 2023

(87) PCT Pub. No.: WO2022/056370
PCT Pub. Date: Mar. 17, 2022

(65) Prior Publication Data
US 2023/0326165 A1     Oct. 12, 2023

Related U.S. Application Data

(60) Provisional application No. 63/077,405, filed on Sep. 11, 2020, provisional application No. 63/077,398, filed on Sep. 11, 2020.

(51) Int. Cl.
*G06T 7/20* (2017.01)
*G06T 7/00* (2017.01)
(Continued)

(52) U.S. Cl.
CPC .............. *G06T 7/0012* (2013.01); *G06T 7/70* (2017.01); *G06V 10/25* (2022.01); *G06V 10/82* (2022.01);
(Continued)

(58) Field of Classification Search
CPC .................... G06T 7/0012; G06T 7/70; G06T 2207/20084; G06T 2207/30044;
(Continued)

(56) References Cited

U.S. PATENT DOCUMENTS 10,646,156 B1 * 5/2020 Schnorr ................. G16H 30/40
2001/0019568 A1    9/2001 Sakata
(Continued)

FOREIGN PATENT DOCUMENTS

CN      102021142 A     4/2011
CN      103339359 A     11/2013
(Continued)

OTHER PUBLICATIONS

Australian Government IP Australia Examination report No. 2 dated Oct. 8, 2024 for corresponding Application No. 2021338858, Applicant names: The Brigham and Women's Hospital, Inc.; The General Hospital Corporation, 4 pages.
(Continued)

*Primary Examiner* — Syed Haider
(74) *Attorney, Agent, or Firm* — Tarolli, Sundheim, Covell & Tummino LLP

(57) ABSTRACT

Systems and methods are provided for determining a clinical parameter representing the location of interest within a reproductive cellular structure. An image of the reproductive
(Continued)

cellular structure is obtained and provided to a neural network to generate the clinical parameter. The clinical parameter is stored on a non-transitory computer readable medium.

19 Claims, 3 Drawing Sheets

(51) Int. Cl.

| | | |
|---|---|---|
| *G06T 7/70* | (2017.01) | |
| *G06V 10/25* | (2022.01) | |
| *G06V 10/82* | (2022.01) | |
| *G06V 20/69* | (2022.01) | |
| *G16H 50/20* | (2018.01) | |

(52) U.S. Cl.
CPC .......... *G06V 20/698* (2022.01); *G16H 50/20* (2018.01); *G06T 2207/20084* (2013.01); *G06T 2207/30044* (2013.01)

(58) Field of Classification Search
CPC ...... G16H 50/20; G06V 10/25; G06V 20/698; G06V 10/82
See application file for complete search history.

(56) References Cited

U.S. PATENT DOCUMENTS

| | | | | |
|---|---|---|---|---|
| 2016/0078275 | A1 | 3/2016 | Wang et al. | |
| 2017/0205390 | A1 | 7/2017 | Shaked et al. | |
| 2019/0073770 | A1* | 3/2019 | Moradi ................... | G06V 10/82 |
| 2019/0195689 | A1 | 6/2019 | McQuilkin et al. | |
| 2020/0117960 | A1 | 4/2020 | Yan et al. | |
| 2020/0210754 | A1 | 7/2020 | Lin et al. | |
| 2020/0226750 | A1 | 7/2020 | Shafiee | |
| 2021/0174154 | A1* | 6/2021 | Duncan ................. | G06T 7/0012 |
| 2021/0319208 | A1* | 10/2021 | Ohara .................... | G06V 10/82 |

FOREIGN PATENT DOCUMENTS

| | | | | |
|---|---|---|---|---|
| CN | 109584211 | A | 4/2019 | |
| CN | 109815851 | A | 5/2019 | |
| CN | 110288037 | A | 9/2019 | |
| JP | 08029594 | A | 2/1996 | |
| JP | 2011004638 | A | 1/2011 | |
| JP | 2014504849 | A | 2/2014 | |
| JP | 2016509845 | A | 4/2016 | |
| JP | 2017092730 | A | 5/2017 | |
| JP | 2018022216 | A | 8/2018 | |
| JP | 2019509057 | A | 4/2019 | |
| JP | 2020036625 | A | 3/2020 | |
| KR | 20100000632 | A | 1/2010 | |
| KR | 20100000632 | U | 1/2010 | |
| WO | 2010128670 | A1 | 11/2010 | |
| WO | 2012150689 | A1 | 8/2012 | |
| WO | 2017184757 | A1 | 10/2017 | |
| WO | WO-2019068073 | A1 * | 4/2019 | .......... G06T 7/0012 |
| WO | 2019211593 | A1 | 11/2019 | |
| WO | 2019225177 | A1 | 11/2019 | |
| WO | 2020138279 | A1 | 2/2020 | |
| WO | 2020068380 | A1 | 4/2020 | |
| WO | 2020157761 | A1 | 8/2020 | |
| WO | 2022056370 | A1 | 3/2022 | |

OTHER PUBLICATIONS

First Canadian Office Action dated Aug. 8, 2024 for corresponding CA application 3,192,441, 4 pages.

Letter from the Japanese Patent Office for Notice of Office Action for Application No. 2023-515551; Applicant The Brigham and Women's Hospital, Inc.; The General Hospital Corporation dated May 6, 2024, 2 pages. Text of the First Office Action English translation provided, 8 pages.

IP Australia Examination Report No. 1 dated Mar. 27, 2024 referencing Australian Patent Application No. 2021338858; Applicant names: The Brigham and Women's Hospital, Inc.; The General Hospital Corporation, 4 pages.

Patent Office of The Russian Federation Office Action to corresponding Application No. 2023108274/14(017882), Filing date: Sep. 13, 2021, Applicant(s): The Brigham and Women's Hospital, Inc., the General Hospital Corporation, US, with a mailing date of May 16, 2024. Text of the Office Action English translation provided, 9 pages.

Russian Patent Search Report Application No. 2023108274/14(017882) with a filing date of Sep. 13, 2021 for invention titled Determining Locations in Reproductive Cellular Structures, pp. 1-2.

Russian Office Action Application No. 2023108274/14(017882) with a filing date of Sep. 13, 2021 for invention titled Determining Locations in Reproductive Cellular Structures, pp. 1-10.

Patent Office of The Russian Federation Office Action for corresponding Application No. 2023108274/14(017882) with a filing date of Sep. 13, 2021; applicants The Brigham and Women's Hospital, Inc., US, the General Hospital Corporation, US., date of mailing Feb. 11, 2023.

Government of India Examination Report dated Apr. 7, 2025; Application No. 202317023723; date of filing Mar. 30, 2023; PCT International Application No. US2021050050 with a date of Sep. 13, 2021; with a date of publication Nov. 24, 2023; 7 pages.

English translation of the preliminary office action report related to Patent Application No. BR112023004565-7 3 pages.

Chavez-Badiola Alejandro et al, "Embryo Ranking Intelligent Classification Algorithm (ERICA): artificial intelligence clinical assistant predicting embryo ploidy and implantation", Reproductive BioMedicine Online, vol. 41, Issue 4, 2020, doi:10.1016/j.rbmo.2020.07.003, (Jul. 5, 2020), pp. 585-593, URL:https://www.sciencedirect.com/science/article/pii/S1472648320303734, (Aug. 19, 2024), XP093197276.

Anonymous, "Ensemble learning—Snapshot", Wikipedia, (Sep. 9, 2020), URL: https://en.wikipedia.org/w/index.php?title=Ensemble_learning&oldid=977473189, (Aug. 22, 2024), XP093197956.

Korean Intellectual Property Office Notice Requesting Submission of Opinion with a delivery date of Sep. 2, 2025; Korean Patent Application No. 10-2023-7012202 with a filing date of Apr. 10, 2023 for Applicant The Brigham and Women's Hospital, Inc. et al., 4 pages.

The State Intellectual Property Office of the People's Republic of China, Notice of First Office Action, with a dispatching date of Nov. 3, 2025 for Application No. 202180075763.0, Applicant The Brigham and Women's Hospital, Inc.; The General Hospital Corporation; 20 pages.

Written Opinion of Intellectual Property Office of Singapore dated Jan. 24, 2026 for corresponding Application No. 11202301731S with an Application filing date of Sep. 13, 2021, 7 pages.

Corresponding Chinese Patent Application No. 202180075763.0, Second Office Action dated Apr. 28, 2026.

* cited by examiner

DETERMINING LOCATIONS IN REPRODUCTIVE CELLULAR STRUCTURES

RELATED APPLICATIONS

The present application claims priority to each of U.S. Provisional Patent Application Ser. No. 63/077,405 filed Sep. 11, 2020 entitled ARTIFICIAL INTELLIGENCE-EN-ABLED SYSTEM TO AID IN ANEUPLOIDY SCREEN-ING OF PREIMPLANTATION EMBRYOS and U.S. Pro-visional Patent Application Ser. No. 63/077,398 filed Sep. 11, 2020 entitled ARTIFICIAL INTELLIGENCE-EN-ABLED SYSTEM FOR ALIGNMENT OF OOCYTES AND PREIMPLANTATION EMBRYOS FOR INTRACY-TOPLASMIC SPERM INJECTION (ICSI) AND ASSISTED HATCHING (AH) PROCEDURES. The entire content of each of these applications is incorporated herein by reference in its entirety for all purposes.

STATEMENT ON GOVERNMENT RIGHTS

This invention was made with government support under one or more of grant numbers R01AI118502, R01AI138800, and R21HD092828, awarded by the National Institutes of Health. The government has certain rights in the invention.

TECHNICAL FIELD

The present invention relates generally to the field of assisted fertility, and more particularly, to determining loca-tions in reproductive cellular structures.

BACKGROUND OF THE INVENTION

Infertility is an underestimated healthcare problem that affects over forty-eight million couples globally and is a cause of distress, depression, and discrimination. Although assisted reproductive technologies (ART) such as in-vitro fertilization (IVF) has alleviated the burden of infertility to an extent, it has been inefficient with an average success rate of approximately twenty-six percent reported in 2015 in the US. IVF remains as an expensive solution, with a cost between $7000 and $20,000 per ART cycle in the US, which is generally not covered by insurance. Further, many patients require multiple cycles of IVF to achieve pregnancy. Embryos are usually transferred to a patient's uterus during either the cleavage or the blastocyst stage of development. Embryos are described as being at the cleavage stage two or three days after fertilization. Embryos reach the blastocyst stage five or six days after fertilization. Blastocysts have fluid filled cavities and two distinguishable cell types, the trophectoderm and the inner cell mass (ICM).

SUMMARY OF THE INVENTION

In accordance with an aspect of the present invention, a system is provided. The system includes a processor and a non-transitory computer readable medium storing machine executable instructions for assigning a value representing a location of interest within a reproductive cellular structure. The machine executable instructions include an imager interface that receives an image of the reproductive cellular structure from an associated imager. A neural network determines a clinical parameter representing the location of interest within the reproductive cellular structure from the image of the reproductive cellular structure. The clinical parameter is stored at the non-transitory computer readable medium.

In accordance with another aspect of the present inven-tion, a method is provided for determining a clinical param-eter representing the location of interest within a reproduc-tive cellular structure. An image of the reproductive cellular structure is obtained and provided to a neural network to generate the clinical parameter. The clinical parameter is stored on a non-transitory computer readable medium.

In accordance with yet another aspect of the present invention, a method is provided for planning an assisted fertility procedure. An image of a reproductive cellular structure is obtained and provided to a neural network to generate a clinical parameter representing a location of interest within the reproductive cellular structure. A proce-dure is performed on the reproductive cellular structure at a location determined according to the clinical parameter.

BRIEF DESCRIPTION OF THE DRAWINGS

The foregoing and other features of the present invention will become apparent to those skilled in the art to which the present invention relates upon reading the following descrip-tion with reference to the accompanying drawings, in which.

DETAILED DESCRIPTION

The two most widely performed and technically challeng-ing micromanipulation procedures conducted in a clinical embryology laboratory are intracytoplasmic sperm injection (ICSI) and assisted hatching (AH). Both procedures are manually performed by highly trained embryologists. Intra-cytoplasmic sperm injection is a procedure that includes alignment of metaphase (MII) oocytes, selection, and immo-bilization of sperm, and injection of sperm at a precise location that does not interfere with the mitotic spindle. The spindle is located adjacent to the extruded polar body and cannot be visualized using bright field microscopy. Assisted hatching is a procedure designed to enable embryo escape from the zona pellucida (ZP). Studies show that AH may increase the chance of pregnancy in older women with repeat IVF failure and in frozen embryo transfer cycles. This procedure is widely used on cleavage stage embryos to facilitate herniation and biopsy of trophectoderm cells for Preimplantation Genetic Testing. Blastomeres can be easily damaged if AH is performed too close to healthy cells.

A "reproductive cellular structure", as used herein, is a single cell or multicellular structure involved in an assisted fertility procedure on a mammalian subject. Reproductive cellular structures can include gametes, such as oocytes, as well as fertilized embryos prior to implantation.

A "static observation," as used herein, is an image or group of images of a reproductive cellular structure that represent a single point in the development of the reproductive cellular structure. Where multiple images are used in a static observation, no discernible change in the structure and appearance of the reproductive cellular structure will have taken place between images.

Figure 1:
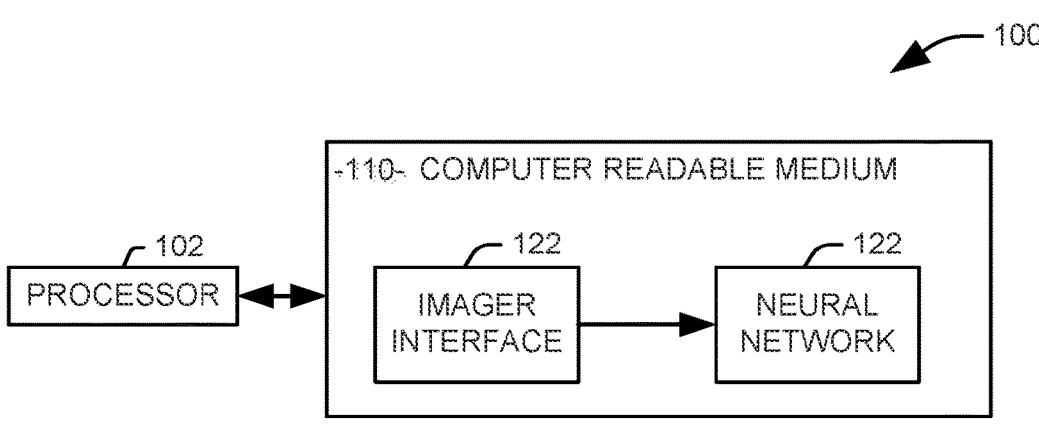
FIG. 1 illustrates one example of a system for determining a location of interest on a reproductive cellular structure.

FIG. 1 illustrates one example of a system 100 for determining a location of interest on a reproductive cellular structure. The system 100 includes a processor 102 and a non-transitory computer readable medium 110 that stores machine executable instructions for assigning a value representing a location of interest within a reproductive cellular structure. The machine executable instructions include an imager interface 112 that receives an image of the reproductive cellular structure from an associated imager. For example, the imaging interface 112 can receive the image from the imager via a bus or network connection and condition the image for analysis at a neural network 114. In one example, the neural network 114 can be implemented on a cloud computing system, with the image transmitted to the server containing the neural network 114 via a network interface (not shown).

The neural network 114 determines, from the image of the reproductive cellular structure, a clinical parameter representing the location of interest within the reproductive cellular structure. In one implementation, each possible value of the categorical clinical parameter represents a designated location within a representation of the reproductive cellular structure. In one example, the representation can be substantially circular, and the various values for the clinical parameter can represent individual sectors of the circle. In one implementation, the representation is divided into twelve thirty-degree sectors. In another example, the representation is divided into an array of tiled polygons, with each polygon in the array being represented by one of the values for the clinical parameter. In one implementation, the reproductive cellular structure is an oocyte and the clinical parameter represents a location of the polar body within the oocyte. In another implementation, the reproductive cellular structure is an embryo and the clinical parameter represents a location on the zona pellucida that is furthest from a healthy blastomere.

The neural network 114 includes a plurality of nodes having a plurality of interconnections. Values from the image, for example luminance and/or chrominance values associated with the individual pixels, are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to an activation function at the node. For example, the intermediate node can sum the received values and subject the sum to an identify function, a step function, a sigmoid function, a hyperbolic tangent, a rectified linear unit, a leaky rectified linear unit, a parametric rectified linear unit, a Gaussian error linear unit, the softplus function, an exponential linear unit, a scaled exponential linear unit, a Gaussian function, a sigmoid linear unit, a growing cosine unit, the Heaviside function, and the mish function. A final layer of nodes provides the confidence values for the output classes of the ANN, with each node having an associated value representing a confidence for one of the associated output classes of the classifier.

Many ANN classifiers are fully-connected and feedforward. A convolutional neural network, however, includes convolutional layers in which nodes from a previous layer are only connected to a subset of the nodes in the convolutional layer. Recurrent neural networks are a class of neural networks in which connections between nodes form a directed graph along a temporal sequence. Unlike a feedforward network, recurrent neural networks can incorporate feedback from states caused by earlier inputs, such that an output of the recurrent neural network for a given input can be a function of not only the input but one or more previous inputs. As an example, Long Short-Term Memory (LSTM) networks are a modified version of recurrent neural networks, which makes it easier to remember past data in memory.

The neural network 114 is trained on a plurality of labeled images of the appropriate reproductive cellular structure. By "labeled images," it is meant that the position of the location of interest within the image is known, for example, via expert annotation, and the clinical parameter associated with the position of the location of interest is provided to the neural network along with the image during the training process. During training, the weights associated with the interconnections among nodes in the neural network 114 are iteratively changed until, once the network is changed, an output of the network when presented with a novel, unlabeled image provides a clinical parameter representing the location of the location of interest within the novel image. This clinical parameter or a representation of the clinical parameter can be stored on the non-transitory computer readable medium 110 and/or provided to a user via an associated output device.

Figure 2:
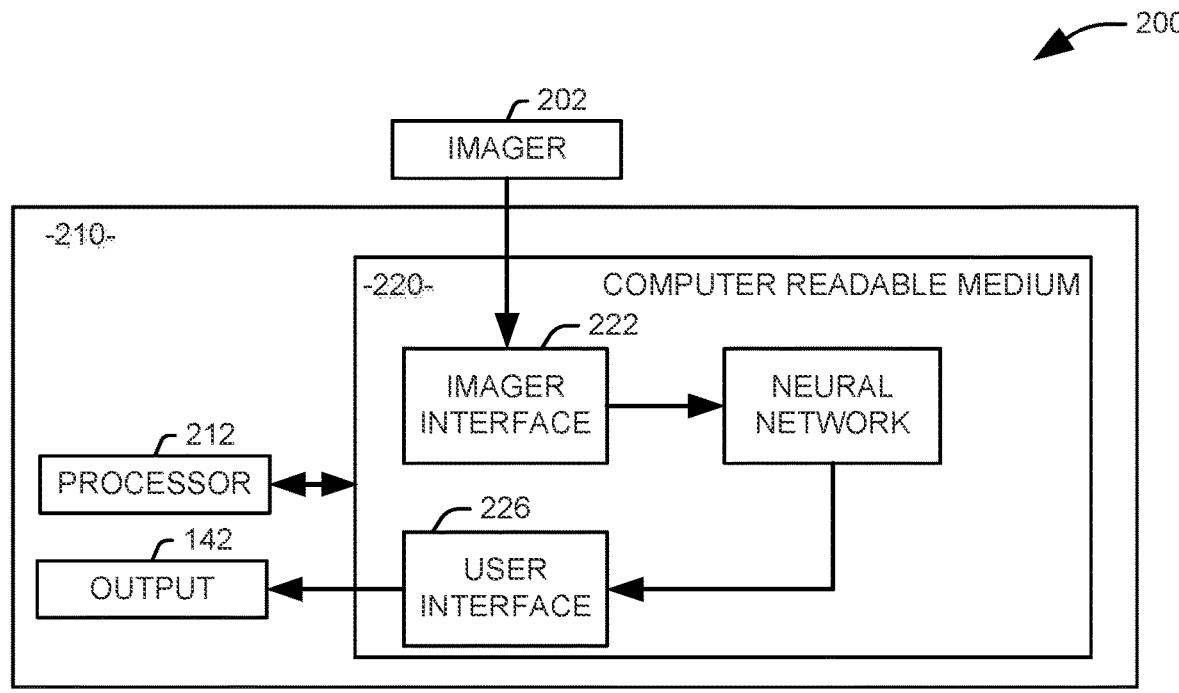
FIG. 2 illustrates another example of a system for deter-mining a location of interest on a reproductive cellular structure.

FIG. 2 illustrates another example of a system 200 for determining a location of interest on a reproductive cellular structure. Specifically, the system 200 generates a categorical clinical parameter representing a location on the reproductive cellular structure. The system 200 includes an imager 202 that acquires an image of the reproductive cellular structure on at least one day of development. For example, the imager 202 can include one or more cameras, capable of producing images in the visible or infrared range, paired with appropriate optics to provide an image of a reproductive cellular structure. In one implementation, the imager 202 can be implemented to capture images of an embryo at multiple days of development as part of a time-lapse embryo imaging system. In another implementation, the imager 202 can be configured to generate a static observation of the reproductive cellular structure as a set of one or more images. In one implementation, the imager 202 includes an attachment for a mobile device that operates with a camera of the mobile device to provide the images of the reproductive cellular structure. The housing for the attachment can be 3-D printed using polylactic acid with dimensions of 82×34×48 mm. An acrylic lens can be included in the housing to provided appropriate magnification for the embryo images.

In another implementation, the imager 202 can be implemented as a stand-alone system with an optical housing that is 3-D printed from polylactic acid and overall dimensions of 62×92×175 mm. The housing contains an electronic circuit with a white light-emitting diode, a three-volt battery, and a single pole double-throw switch. The embryo sample is transilluminated, with a 10× Plan-Achromatic objective lens for image magnification and a complementary metal-oxide-semiconductor (CMOS) image sensor for embryo image data acquisition. The CMOS sensor can be connected to a single-board computer to process the captured images.

The imager 202 can be connected to a mobile device via a wireless connection (e.g., Wi-Fi, Bluetooth, or a similar connection) for data processing and visualization.

The one or more images obtained at the imager 202 are provided to an analysis system 210 comprising a processor 212, an output device 214, and a non-transitory computer readable medium 220 storing instructions executable by the processor. The instructions are executable to provide an imager interface 222 that receives the image or images of the reproductive cellular structure. The imager interface 222 can apply one or more imaging condition techniques, such as cropping and filtering, to better prepare the image for analysis. The images are then provided to a neural network 224 that provides the categorical clinical parameter representing the desired location.

In one implementation, the neural network 224 can be a convolutional neural network, which is a feed-forward artificial neural network that includes convolutional layers, which effectively apply a convolution to the values at the preceding layer of the network to emphasize various sets of features within an image. In a convolutional layer, each neuron is connected only to a proper subset of the neurons in the preceding layer, referred to as the receptive field of the neuron. In one example, the convolutional neural network is implemented using the Xception architecture. In one implementation, at least one chromatic value (e.g., a value for an RGB color channel, a YCrCb color channel, or a grayscale brightness) associated with each pixel is provided as an initial input to the convolutional neural network.

In another implementation, the neural network 224 can be implemented as a recurrent neural network. In a recurrent neural network, the connections between nodes in the network are selected to form a directed graph along a sequence, allowing it to exhibit dynamic temporal behavior. In another implementation, the neural network 224 is implemented and trained as a discriminative network in a generative adversarial model, in which a generative neural network and the discriminative network provide mutual feedback to one another, such that the generative neural network produces increasingly sophisticated samples for the discriminative network to attempt to classify. Regardless of the structure of the neural network 224, some or all layers of the neural network can be trained via transfer learning from another system, with only some of the layers trained on the training images of the reproductive cellular structure. A final layer of the neural network 224 can be implemented as a softmax layer to provide a classification result.

In response to a novel image, the neural network 224 generates a clinical parameter representing the portion of the image containing the location of interest. The clinical parameter can be provided to a user at the output device 214 via a user interface 226. For example, the user interface 226 can include appropriate software instructions for receiving the output of the neural network 224 and presenting it at the output device 214. In one implementation, the output device 214 can include a mobile device that communicates wirelessly with the analysis system 210. In one example, the clinical parameter can be provided to the user as a representation of the cellular reproductive structure with the section of the cellular reproductive structure highlighted within the representation.

Figure 3:
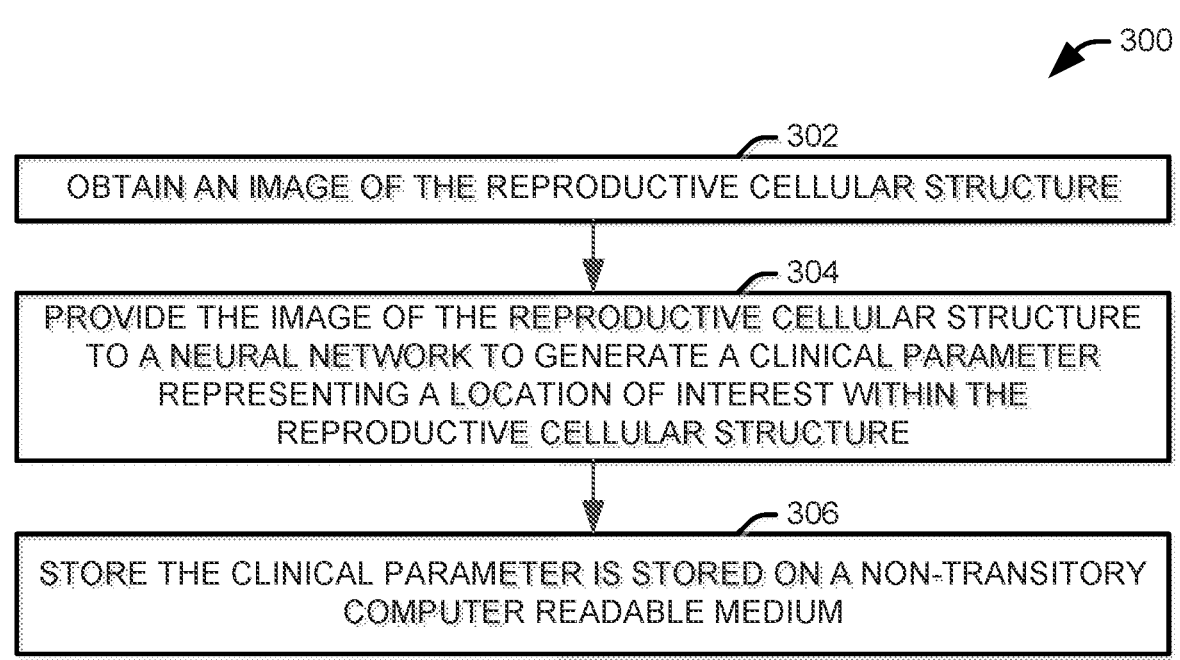
FIG. 3 illustrates a method for determining a clinical parameter representing the location of interest within a reproductive cellular structure
Figure 4:
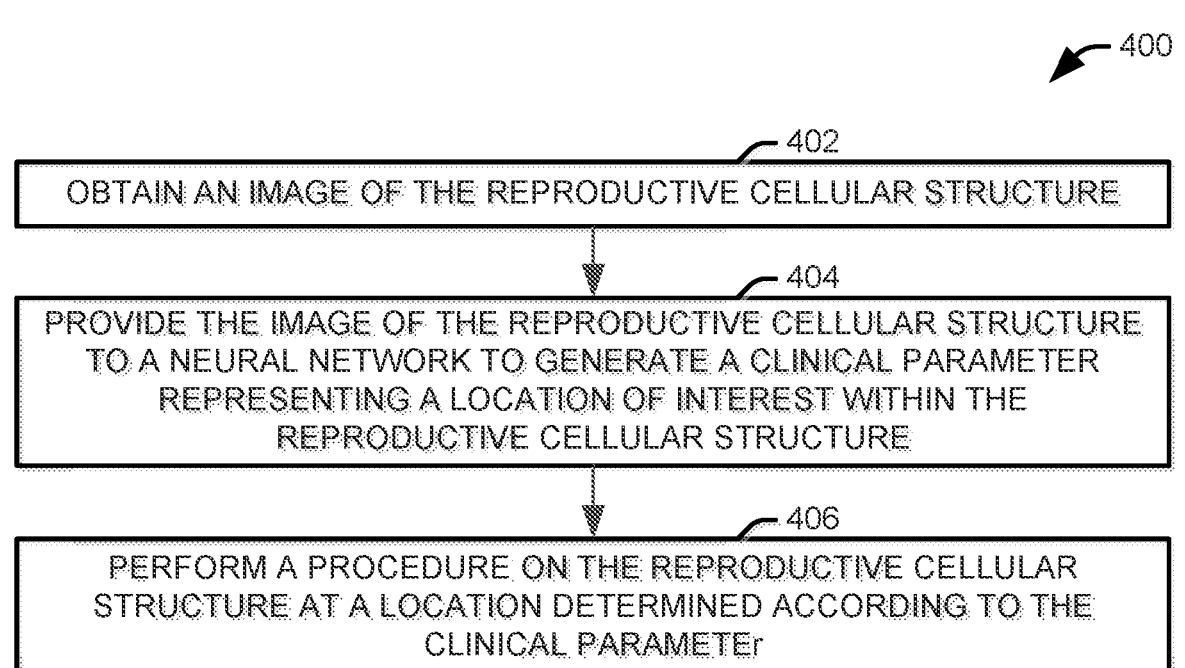
FIG. 4 illustrates a method for planning an assisted fertility procedure.

In view of the foregoing structural and functional features described above, a method in accordance with various aspects of the present invention will be better appreciated with reference to FIGS. 3 and 4. While, for purposes of simplicity of explanation, the methods of FIGS. 3 and 4 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method in accordance with an aspect the present invention.

FIG. 3 illustrates one method 300 for determining a clinical parameter representing the location of interest within a reproductive cellular structure. In one example, the method 300 can be used to determine the location of a polar body within an oocyte, with the clinical parameter representing a portion of the oocyte containing the polar body. In another example, the method can be used to determine a location on the zona pellucida that is furthest from a healthy blastomere, with the clinical parameter representing the appropriate location. At 302, an image of the reproductive cellular structure is obtained. For example, an image can be captured at an appropriate imager and provided to a computer system for image processing.

At 304, the image of the reproductive cellular structure is provided to a neural network to generate the clinical parameter. Each possible value of the clinical parameter represents a designated location within a representation of the reproductive cellular structure, such that the clinical parameter indicates the location of interest within the image. The neural network can be implemented as any of a convolutional neural network, a recurrent neural network, and a discriminative classifier trained as part of a generative adversarial network. At 306, the clinical parameter is stored on a non-transitory computer readable medium.

FIG. 4 illustrates a method 400 for planning an assisted fertility procedure. At 402, an image of the reproductive cellular structure is obtained. For example, an image can be captured at an appropriate imager and provided to a computer system for image processing. At 404, the image of the reproductive cellular structure is provided to a neural network to generate a clinical parameter representing a location of interest within the reproductive cellular structure. Each possible value of the clinical parameter represents a designated location within a representation of the reproductive cellular structure, such that the clinical parameter indicates the location of interest within the image. The neural network can be implemented as any of a convolutional neural network, a recurrent neural network, and a discriminative classifier trained as part of a generative adversarial network.

At 406, a procedure can be performed on the reproductive cellular structure at a location determined according to the clinical parameter. In one example, the method 400 can be used to determine the location of a polar body within an oocyte, with the clinical parameter representing a portion of the oocyte containing the polar body. The location of the polar body can be used to determine an appropriate location for intracytoplasmic sperm injection. For example, the intracytoplasmic sperm injection can be performed at a location spaced ninety degrees from the polar body. In another example, the method 400 can be used to determine a location on the zona pellucida that is furthest from a healthy blastomere to avoid damaging healthy blastomeres during laser assisted hatching. In one implementation, the procedure can be performed by an automated robotic system based upon the location represented by the clinical parameter.

Figure 5:
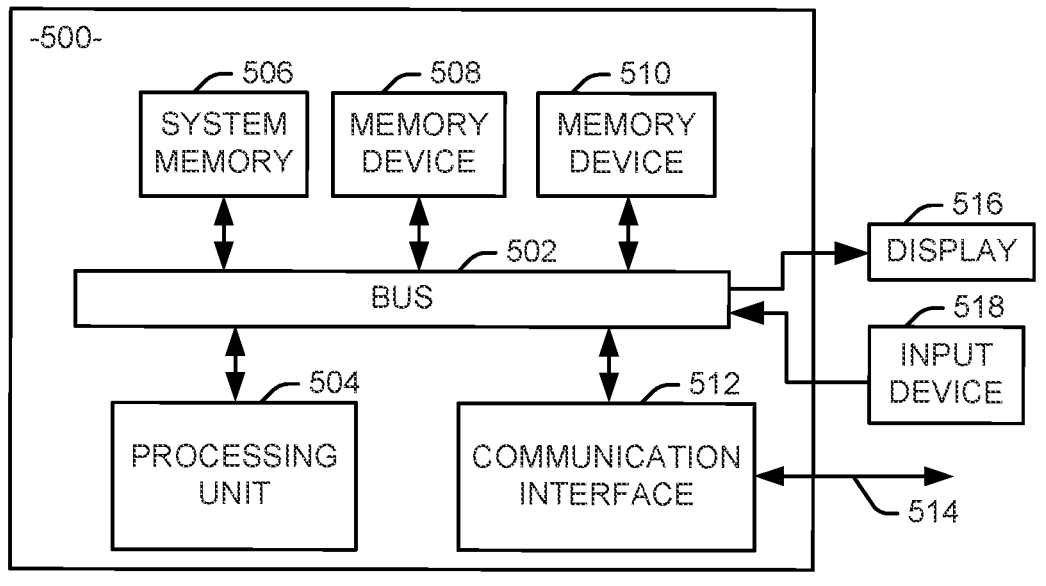
FIG. 5 is a schematic block diagram illustrating an exemplary system of hardware components capable of implementing examples of the systems and methods dis-closed herein.

FIG. 5 is a schematic block diagram illustrating an exemplary system 500 of hardware components capable of implementing examples of the systems and methods disclosed in FIGS. 1-4, such as the systems illustrated in FIGS. 1 and 2. The system 500 can include various systems and subsystems. The system 500 can be any of personal computer, a laptop computer, a workstation, a computer system, an appliance, an application-specific integrated circuit (ASIC), a server, a server blade center, or a server farm.

The system 500 can includes a system bus 502, a processing unit 504, a system memory 506, memory devices 508 and 510, a communication interface 512 (e.g., a network interface), a communication link 514, a display 516 (e.g., a video screen), and an input device 518 (e.g., a keyboard and/or a mouse). The system bus 502 can be in communication with the processing unit 504 and the system memory 506. The additional memory devices 508 and 510, such as a hard disk drive, server, stand-alone database, or other non-volatile memory, can also be in communication with the system bus 502. The system bus 502 interconnects the processing unit 504, the memory devices 506-510, the communication interface 512, the display 516, and the input device 518. In some examples, the system bus 502 also interconnects an additional port (not shown), such as a universal serial bus (USB) port.

The system 500 could be implemented in a computing cloud. In such a situation, features of the system 500, such as the processing unit 504, the communication interface 512, and the memory devices 508 and 510 could be representative of a single instance of hardware or multiple instances of hardware with applications executing across the multiple of instances (i.e., distributed) of hardware (e.g., computers, routers, memory, processors, or a combination thereof). Alternatively, the system 500 could be implemented on a single dedicated server.

The processing unit 504 can be a computing device and can include an application-specific integrated circuit (ASIC). The processing unit 504 executes a set of instructions to implement the operations of examples disclosed herein. The processing unit can include a processing core.

The additional memory devices 506, 508, and 510 can store data, programs, instructions, database queries in text or compiled form, and any other information that can be needed to operate a computer. The memories 506, 508 and 510 can be implemented as computer-readable media (integrated or removable) such as a memory card, disk drive, compact disk (CD), or server accessible over a network. In certain examples, the memories 506, 508 and 510 can comprise text, images, video, and/or audio, portions of which can be available in formats comprehensible to human beings.

Additionally or alternatively, the system 500 can access an external data source or query source through the communication interface 512, which can communicate with the system bus 502 and the communication link 514.

In operation, the system 500 can be used to implement one or more parts of an embryo evaluation system in accordance with the present invention. Computer executable logic for implementing the composite applications testing system resides on one or more of the system memory 506, and the memory devices 508, 510 in accordance with certain examples. The processing unit 504 executes one or more computer executable instructions originating from the system memory 506 and the memory devices 508 and 510. It will be appreciated that a computer readable medium can include multiple computer readable media each operatively connected to the processing unit.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The terms "computer readable medium" and "machine readable medium" includes, but is not limited to portable or fixed storage devices, optical storage devices, wireless channels, and/or various other storage mediums capable of storing that contain or carry instruction(s) and/or data. It will be appreciated that a "computer readable medium" or "machine readable medium" can include multiple media each operatively connected to a processing unit. In such a case, when it is stated that data is stored at the computer readable medium, it can refer to any of the interconnected media within the system.

While the principles of the disclosure have been described above in connection with specific apparatuses and methods, it is to be clearly understood that this description is made only by way of example and not as limitation on the scope of the disclosure.

Having described the invention, we claim:

1. A system comprising:
a processor; and
a non-transitory computer readable medium storing machine executable instructions for assigning a value representing a location of interest within a reproductive cellular structure, the machine executable instructions comprising:
an imager interface that receives an image of the reproductive cellular structure from an associated imager; and
a neural network that determines, from the image of the reproductive cellular structure, a clinical parameter representing the location of interest within the reproductive cellular structure, the neural network being trained on a set of images, each image labelled with one class of a plurality of classes, with each of the plurality of classes representing one section of a plurality of sections comprising the reproductive cellular structure; and
wherein the clinical parameter is a categorical parameter representing the section of the plurality of sections that contains the location of interest within the reproductive cellular structure as one of the plurality of classes, the clinical parameter being stored at the non-transitory computer readable medium.

2. The system of claim 1, further comprising an output device, the machine executable instructions comprising a user interface that displays the clinical parameter to a user at the output device.

3. The system of claim 1, wherein the reproductive cellular structure is an oocyte and the clinical parameter represents a location of the polar body within the oocyte.

4. The system of claim 1, wherein the reproductive cellular structure is an embryo and the clinical parameter represents a location on the zona pellucida that is furthest from a healthy blastomere.

5. The system of claim 1, wherein the neural network is a convolutional neural network.

6. The system of claim 1, further comprising the imager, the imager comprising:
a white light emitting diode;
a complementary metal-oxide-semiconductor (CMOS) image sensor; and
an objective lens connected to the CMOS image sensor.

7. The system of claim 6, further comprising the imager, the imager comprising a plastic housing containing an acrylic lens and configured to affix to a mobile device, such that the acrylic lens is aligned with a camera of the mobile device.

8. A method for determining a clinical parameter representing a location of interest within a reproductive cellular structure, the method comprising:
obtaining an image of the reproductive cellular structure; and
providing the image of the reproductive cellular structure to a neural network to generate the clinical parameter, the neural network being trained on a set of images, each image labelled with one class of a plurality of classes, with each of the plurality of classes representing one section of a plurality of sections comprising the reproductive cellular structure and the clinical parameter representing being a categorical parameter representing the section of the plurality of sections that contains the location of interest within the reproductive cellular structure as one of the plurality of classes; and
storing the clinical parameter on a non-transitory computer readable medium.

9. The method of claim 8, further comprising performing a procedure on the reproductive cellular structure at a location determined according to the clinical parameter.

10. The method of claim 9, wherein the procedure on the reproductive cellular structure is one of intracytoplasmic sperm injection and laser assisted hatching.

11. The method of claim 8, wherein the reproductive cellular structure is an oocyte and the clinical parameter represents a location of the polar body within the oocyte.

12. The method of claim 8, wherein the reproductive cellular structure is an embryo and the clinical parameter represents a location on the zona pellucida that is furthest from a healthy blastomere.

13. The method of claim 8, wherein providing the image of the embryo to the neural network comprises providing the image of the embryo to a discriminative classifier trained as part of a generative adversarial network.

14. The method of claim 8, wherein providing the image of the embryo to the neural network comprises providing the image of the embryo to a recurrent neural network.

15. A method for planning an assisted fertility procedure, the method comprising:
obtaining an image of a reproductive cellular structure; and
providing the image of the reproductive cellular structure to a neural network to generate a clinical parameter representing a location of interest within the reproductive cellular structure, the neural network being trained on a set of images, each image labelled with one class of a plurality of classes, with each of the plurality of classes representing one section a plurality of sections comprising of the reproductive cellular structure and the clinical parameter being a categorical parameter representing the section of the plurality of sections that contains the location of interest within the reproductive cellular structure as one of the plurality of classes; and
performing a procedure on the reproductive cellular structure at a location determined according to the clinical parameter.

16. The method of claim 15, wherein the reproductive cellular structure is an oocyte and the clinical parameter represents a location of the polar body within the oocyte.

17. The method of claim 16, wherein performing a procedure on the reproductive cellular structure at the location determined according to the clinical parameter comprises performing intracytoplasmic sperm injection at a location spaced ninety degrees from the polar body.

18. The method of claim 15, wherein the reproductive cellular structure is an embryo and the clinical parameter represents a location on the zona pellucida that is furthest from a healthy blastomere.

19. The method of claim 18, wherein performing a procedure on the reproductive cellular structure at the location determined according to the clinical parameter comprises performing laser assisted hatching at a location indicated by the clinical parameter.

* * * * *